(12) United States Patent
Einstein, Jr. et al.

(10) Patent No.: US 7,243,663 B1
(45) Date of Patent: Jul. 17, 2007

(54) FLOSS DISPENSER CAP

(75) Inventors: J. Lyle Einstein, Jr., Brooklyn, NY (US); John William Colby, Oak Ridge, NC (US); Thomas A. Lockwood, Clemmons, NC (US)

(73) Assignee: Rock-Tenn Shared Services, LLC, Norcross, GA (US)

( * ) Notice: Subject to any disclaimer, the term of this patent is extended or adjusted under 35 U.S.C. 154(b) by 252 days.

(21) Appl. No.: 10/706,740

(22) Filed: Nov. 12, 2003

Related U.S. Application Data

(60) Provisional application No. 60/425,838, filed on Nov. 12, 2002.

(51) Int. Cl.
*A61C 15/04* (2006.01)

(52) U.S. Cl. .................. 132/314; 132/325; 222/93; 222/106; 222/192

(58) Field of Classification Search .............. 132/321, 132/324, 325, 314, 315; 215/328, 384; 222/192, 222/93, 106
See application file for complete search history.

(56) References Cited

U.S. PATENT DOCUMENTS

| | | | |
|---|---|---|---|
| 1,439,076 A | 12/1922 | Edwards | |
| 1,466,982 A | 9/1923 | Bailey | |
| 1,488,810 A | 4/1924 | Fraser | |
| 1,492,838 A | 5/1924 | Decker | |
| 1,614,260 A | 1/1927 | Stewert | |
| 1,733,114 A * | 10/1929 | Brennan | 132/314 |
| 1,858,134 A | 5/1932 | Booth et al. | |
| 4,428,389 A * | 1/1984 | Sanchez Cordero | 132/325 |
| 4,724,855 A * | 2/1988 | Jackson et al. | 134/93 |
| 4,796,783 A * | 1/1989 | Paulson | 222/80 |
| 4,827,951 A * | 5/1989 | Grussmark | 132/314 |
| 5,076,302 A * | 12/1991 | Chari | 132/325 |
| 5,732,722 A * | 3/1998 | Mortvedt | 132/325 |
| 5,979,706 A * | 11/1999 | Grussmark | 222/93 |
| 6,547,104 B1 | 4/2003 | Wilkinson | |

* cited by examiner

Primary Examiner—Cary E. O'Connor
(74) Attorney, Agent, or Firm—Kilpatrick Stockton LLP

(57) ABSTRACT

A dental floss dispenser cap for attachment to a toothpaste tube. The dental floss dispenser cap according to certain embodiments of the invention, comprises a housing and an annular base. Upstanding walls form a cylindrical protrusion and a cavity dimensioned to receive the cap of a toothpaste tube underneath. A spool of floss may be placed on the cylindrical protrusion for rotation and dispensing. A cover may be attached to the housing by a first hinge. The cover preferably comprises a notch opening for the dental floss to pass through and a metal cutting member such as a lance mounted to the cover. A lid may be attached to the cover by a second hinge. The lid can be opened and closed to access the dental floss and protect it from contamination when not in use as desired.

20 Claims, 11 Drawing Sheets

FLOSS DISPENSER CAP

RELATED APPLICATIONS

This application claims priority to U.S. Provisional Application No. 60/425,838 filed on Nov. 12, 2002.

FIELD OF THE INVENTION

The invention relates generally to a dispenser for dental floss and more particularly to a dispenser for dental floss capable of being attached to a tube of toothpaste.

BACKGROUND

Oral hygiene is a significant concern to many individuals. It is common practice for many to brush their teeth twice a day, once in the morning and once in the evening. Another important oral hygiene step is dental flossing. While teeth brushing may remove plaque formed on the surface of the teeth, dental floss assists in removing plaque that may form in between adjacent teeth. Regular flossing may greatly decrease the likelihood of certain gum diseases, such as gingivitis and other periodontal disease that may jeopardize the health of the teeth and even cause tooth loss.

Despite its clear benefits to oral health, flossing is not as commonly practiced as regular teeth brushing. Toothpaste and toothbrush sales typically far outweigh the sales figures for dental floss. This may be partly due to the more recent understanding by the general public of the advantages of flossing and the inconvenience of having to purchase another oral hygiene item. Therefore, a combined dental floss and toothpaste item would be beneficial and convenient for users.

There have been previous attempts to combine dental floss with toothpaste for sale as a single product. For example, U.S. Pat. No. 4,428,389 discloses a floss dispenser adapted to fit onto a tube of toothpaste. Problems arise with respect to hygiene of the floss in such an arrangement. For example, a portion of the dental floss exits the side of the housing and is exposed when not in use. Because toothpaste tubes are typically kept in medicine cabinets, drawers, or on the sink, the exposed floss is likely to be contaminated by dust or other debris.

SUMMARY

The standard toothpaste tube comprises a flexible body containing the toothpaste, a cylindrical opening for discharging the toothpaste, and a cap to seal the toothpaste tube. One common design of toothpaste tubes is to have threads located on the outside of the cylindrical opening and a fluted cap with internal mating threads. Such a toothpaste tube may be opened by unscrewing the toothpaste cap from the rest of the tube, allowing access to the toothpaste.

Certain embodiments of the present invention provide a floss dispenser cap that is easy to use in conjunction with standard toothpaste tubes. The floss dispenser cap provides an ergonomically designed housing that is easy to use for dispensing floss and accessing toothpaste. The ergonomically designed housing comprises a hand friendly shape that allows users to easily hold the dispenser cap or remove the dispenser cap. The dispenser cap may be twisted to unscrew the attached fluted cap from the tube to access the toothpaste.

More particularly described, the floss dispenser cap of certain embodiments of the present invention provides a cap formed of plastic material such as polypropylene, but other suitable plastic materials may also be used. The dispenser cap is preferably designed to snap fit or friction fit onto the cap of a toothpaste tube. The dispenser cap comprises a flip top lid that, when closed, seals the dental floss inside the dispenser cap and protects it from contamination. Inside the dispenser cap, the floss is located on a spool. A dispenser cover is located above the spool and comprises a notch for accessing the floss from the spool. A lance, preferably located on the dispenser cover, may be used to cut the desired amount of floss for use.

According to certain embodiments of the invention, the cover may be attached to the cap by a first hinge. Once the floss is placed inside the cap, the cover may be secured shut. The dental floss may be accessed through the notch. The flip top lid may preferably be attached to the cover by a second hinge. The lid can be opened and closed as desired to access the dental floss.

The floss dispenser cap is preferably designed so that, when the lid is closed, the toothpaste tube may be placed on a flat surface with dispenser cap facing downward. This allows the toothpaste tube to stand up and occupy less space on the surface, such as a bathroom countertop. The floss dispenser cap also reduces clutter in bathrooms and medicine cabinets by combing two oral hygiene products in one package.

DETAILED DESCRIPTION

Certain embodiments of the present invention comprise a floss dispenser that may preferably be attached to a standard type toothpaste tube having a flexible body and fluted cap. It should be understood that certain embodiments of the present invention may be modified to be attached to a toothpaste tube having any type of body and cap. The toothpaste and floss dispenser may be sold together, promoting dental hygiene and convenience for users. The floss dispenser may also be sold separately from toothpaste so that, for example if the user exhausts the dental floss before the toothpaste is consumed, the user may simply buy a new floss dispenser and replace the old one.

Figure 1:
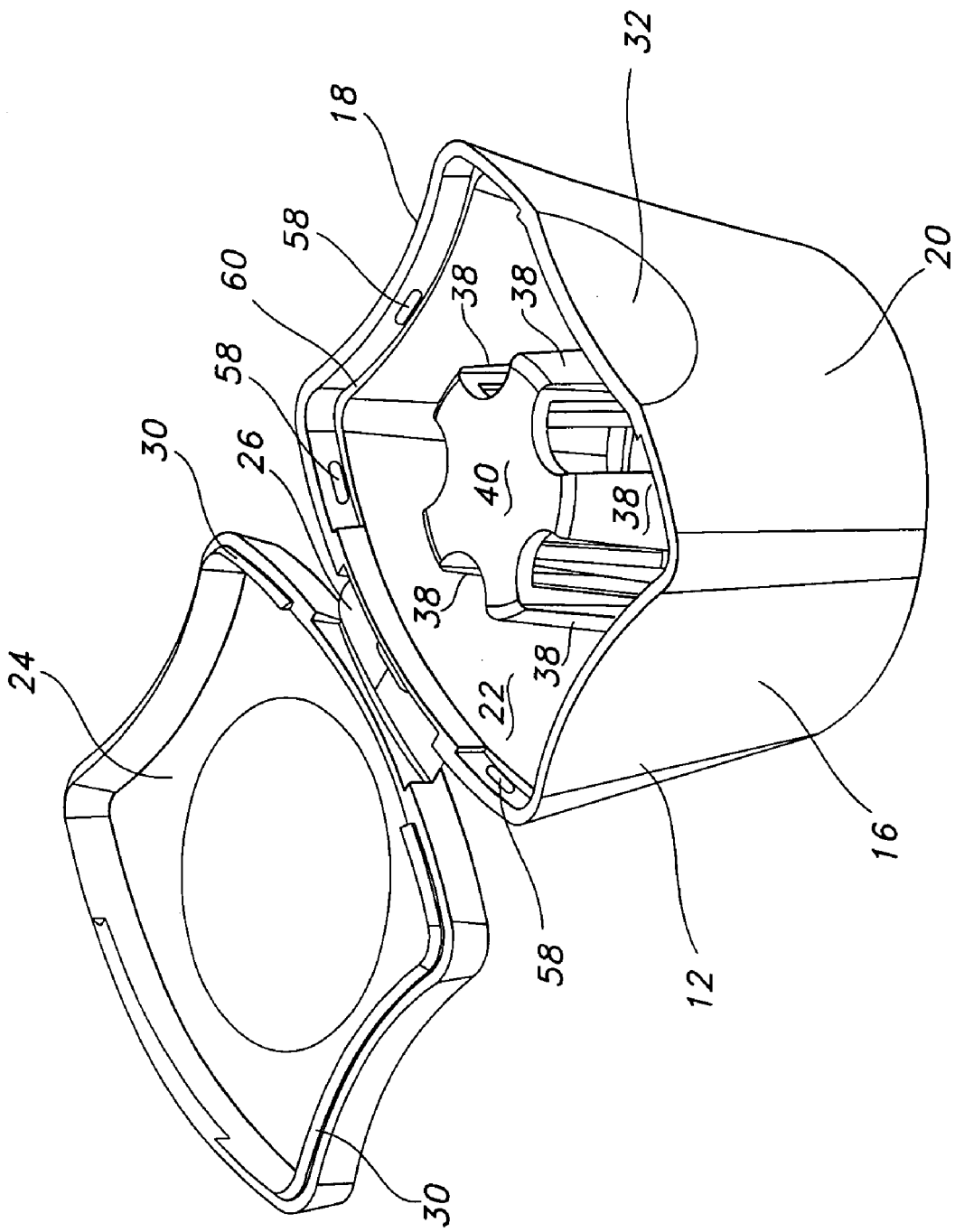
FIG. 1 is a perspective view of a dispenser cap according to certain embodiments of the present invention.
Figure 8:
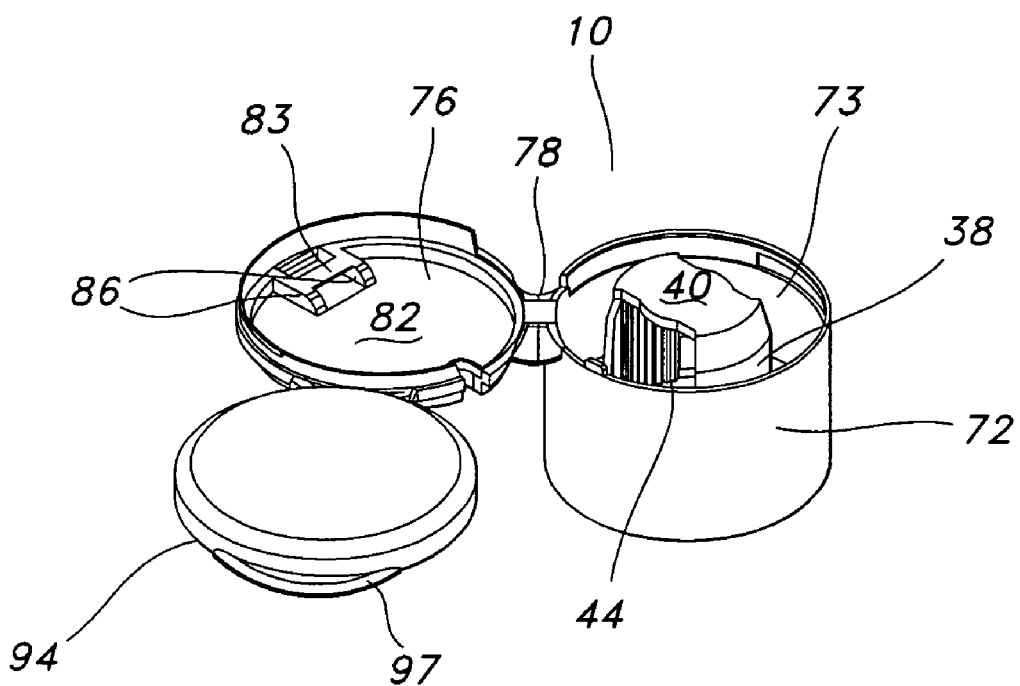
FIG. 8 is a perspective view of a dispenser cap according to certain embodiments of the invention.
Figure 9:
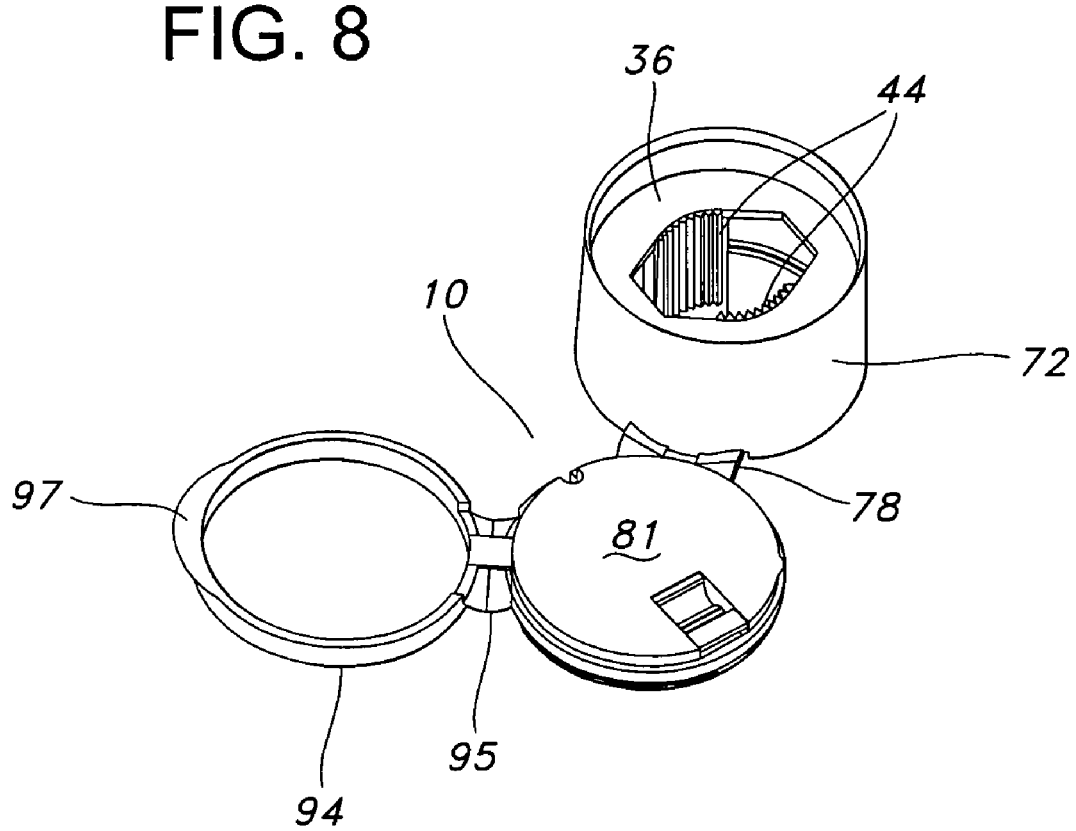
FIG. 9 is a perspective view of the bottom of a dispenser cap according to certain embodiments of the invention.
Figure 10:
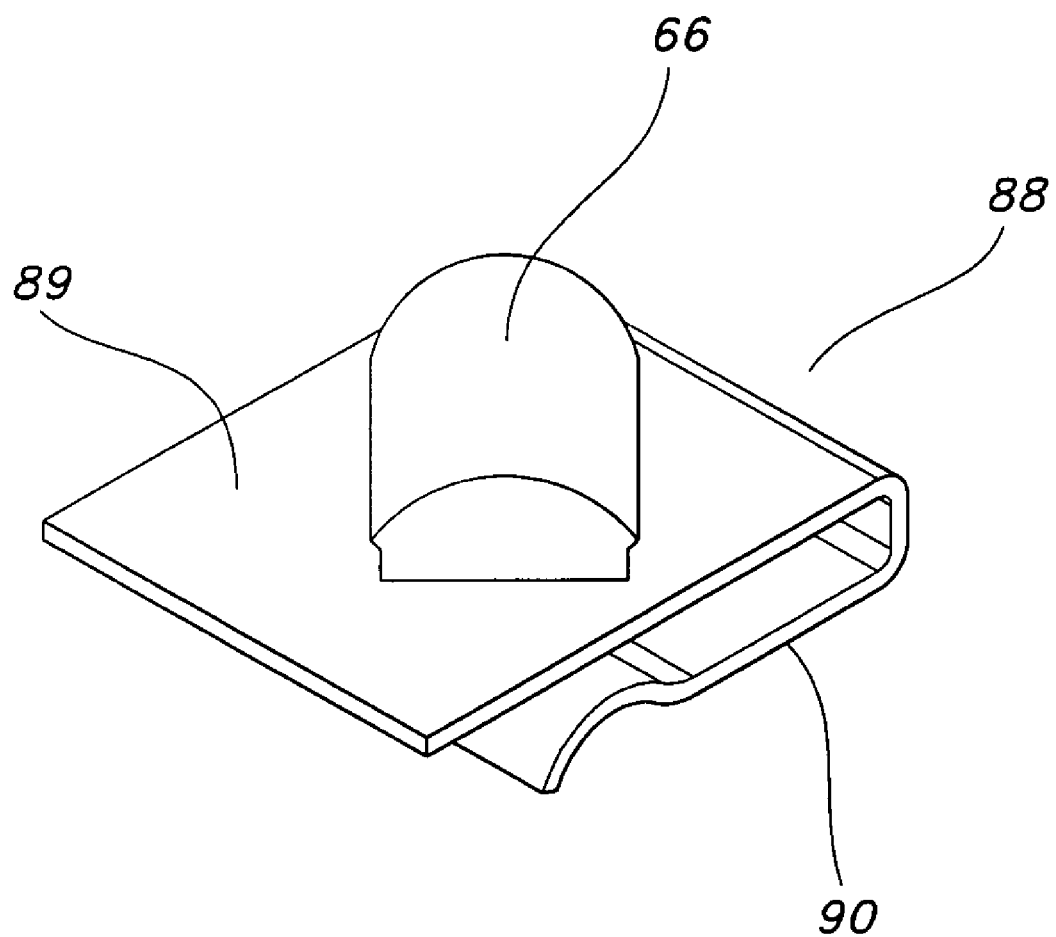
FIG. 10 is a perspective view of a clip comprising a lance according to certain embodiments of the invention.
Figure 11:
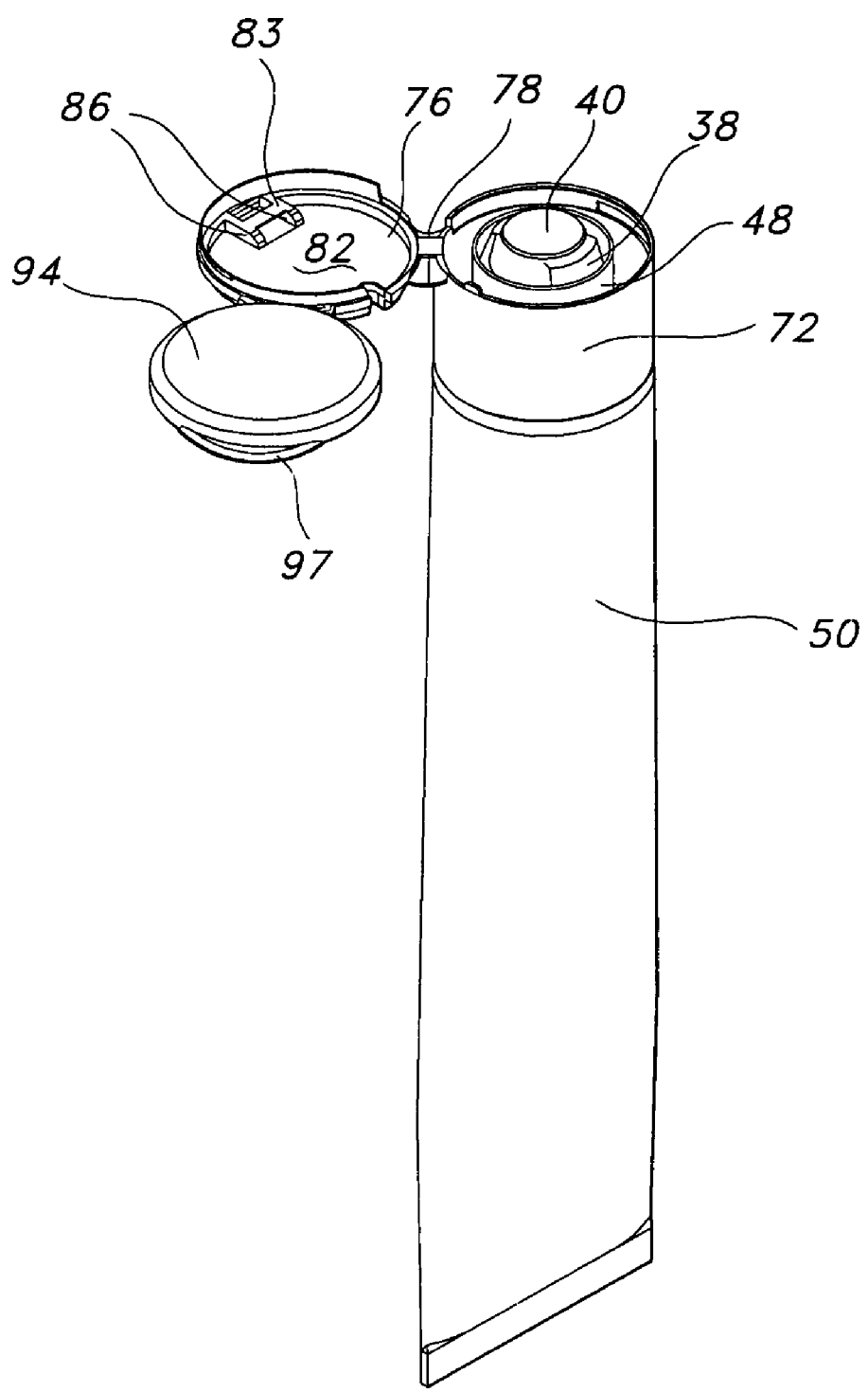
FIG. 11 is a perspective view of a dispenser cap attached to a toothpaste tube according to certain embodiments of the invention.
Figure 12:
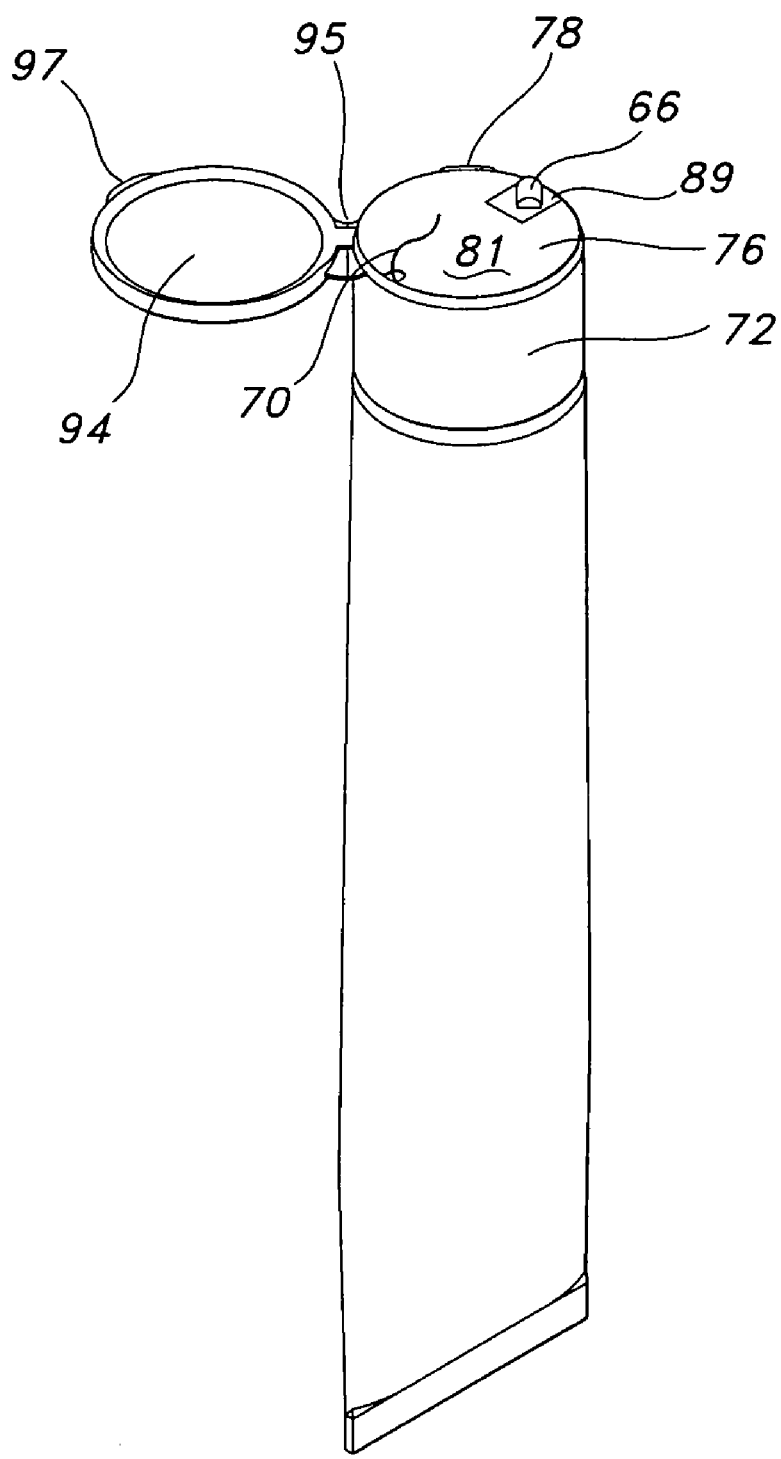
FIG. 12 is a perspective view of a dispenser cap attached to a toothpaste tube according to certain embodiments of the invention.

According to certain embodiments of the present invention, the floss dispenser cap is made from a moldable plastic material such as polypropylene, but other suitable materials may also be used. As shown in FIG. 1, the floss dispenser cap 10 comprises a housing 12 having exterior walls. In the embodiment shown in FIG. 1, the dispenser cap comprises four exterior walls. The two side walls 16, 18 are curved inward to provide users with a convenient place to put their fingers and thumbs when manipulating the dispenser cap. The front wall 20 and back wall 22 are curved outward. The housing, so designed, is hand friendly, making it easy for users to use the floss dispenser cap as described below. According to certain embodiments of the invention, the housing may be cylindrical, as shown in FIGS. 8 and 9, allowing the cap to be easily removed due to the larger diameter of the dispenser as compared to a toothpaste tube cap.

The dispenser cap according to certain embodiments of the present invention comprises a lid 24. The lid is preferably attached to the rear wall of the dispenser cap along a plastic hinge 26. An upstanding ridge 30 is located along the periphery of the inside portion of the lid 24. The ridge causes the lid to snap shut when closed. When the lid is closed along the hinge, pressure applied to the top of the cap causes the ridge to engage the top inside portion the housing walls, creating a friction fit. A concave surface 32 located on the top portion of the front wall of the housing allows users to easily open the flip top lid and gain access to the dental floss (not shown in FIG. 1). The lid is preferably opened by placing the users thumb on the concave surface and applying upward pressure to the lid, releasing the friction fit.

Figure 2:
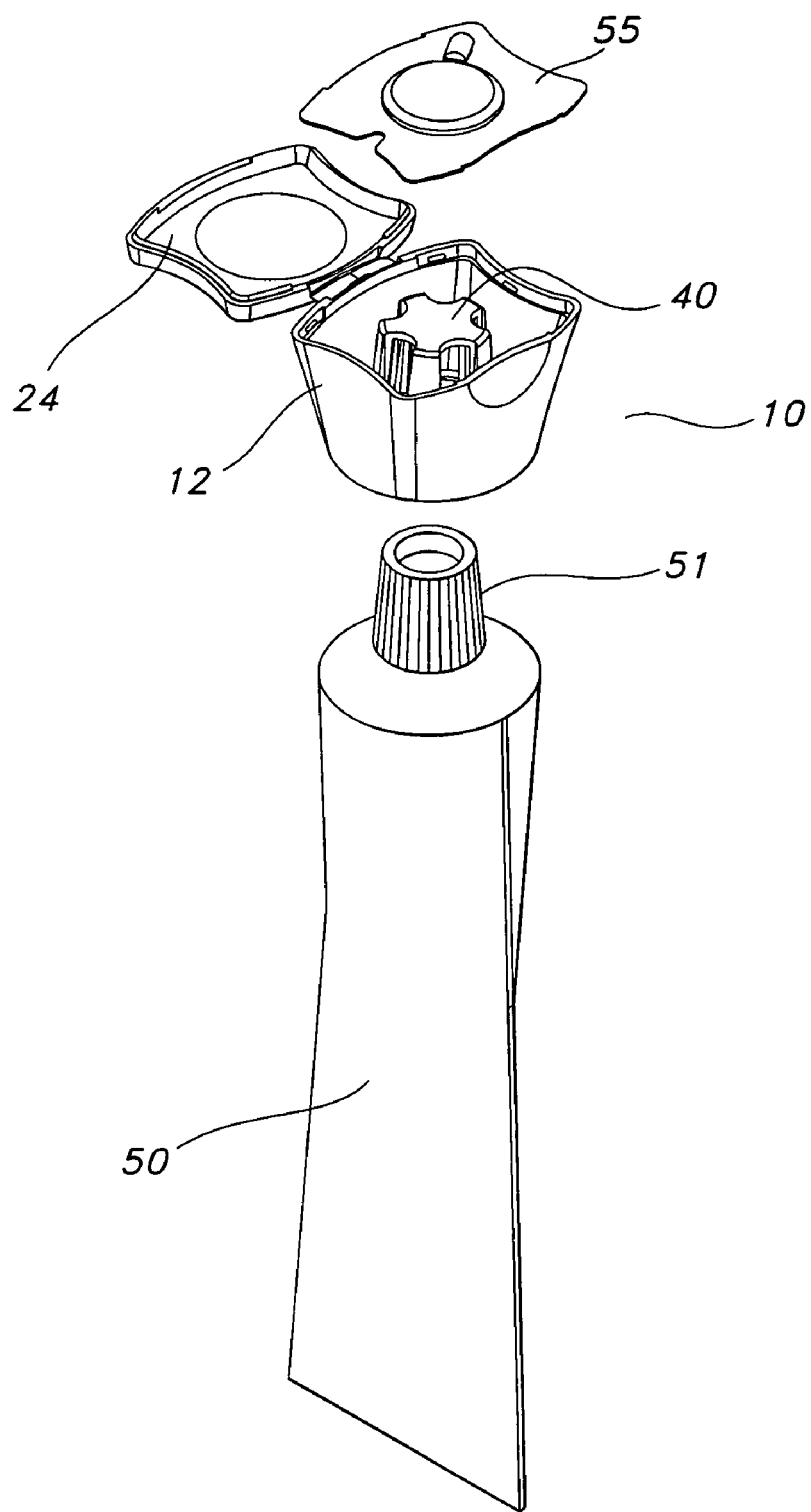
FIG. 2 is an exploded view of a dispenser cap of the present invention and a toothpaste tube.
Figure 3:
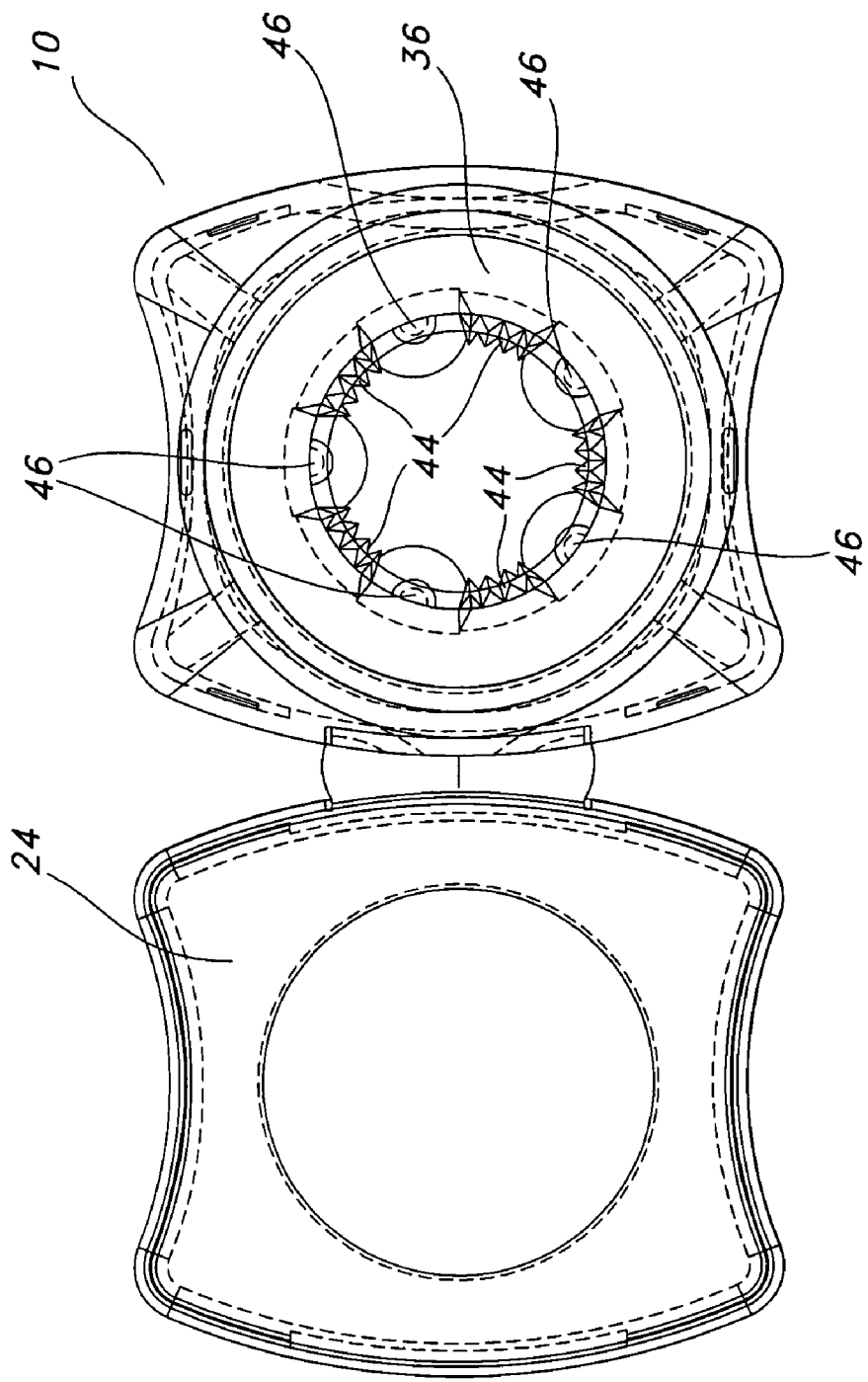
FIG. 3 is a bottom plan view of a dispenser cap according to certain embodiments of the present invention.

According to certain embodiments of the present invention, the interior of the dispenser cap comprises an approximately annular base surface 36. Five upstanding walls extend from the inner edge of the annular surface 36, according to certain embodiments of the invention and as shown in FIG. 3. The upstanding walls are preferably spaced apart equally. The upstanding walls are connected at the top by a flat surface 40, which may approximate the shape of a star. The upstanding walls and the top surface form a cylindrical type protrusion in the interior of the housing. The cylindrical protrusion provides a cavity of approximately the shape of the tooth past tube cap, allowing the dispenser cap to fit on top of the toothpaste tube. The walls are preferably angled slightly inwardly to conform to the shape of the fluted cap 51, as shown in FIG. 2. The cylindrical protrusion provides a cavity of approximately the shape of the toothpaste tube cap, allowing the dispenser cap to fit on top of the toothpaste tube. It should be understood that the cylindrical protrusion may be formed in other manners, for example with a single cylindrical wall and configured to form a cavity for accommodating any type of toothpaste cap. Furthermore, the flat surface on top of the cylindrical protrusion may be any shape that covers the cylinder, or the cylinder may not be covered at all as described below.

The interior of the cylindrical protrusion is preferably hollow. Small ribs 44 line the inside of the upstanding walls of the cylindrical protrusions. The inner edge of the annular base surface may preferably comprises five pressure tabs 46 that extend slightly into the hollow interior of the cylindrical protrusion between the walls.

Figure 4:
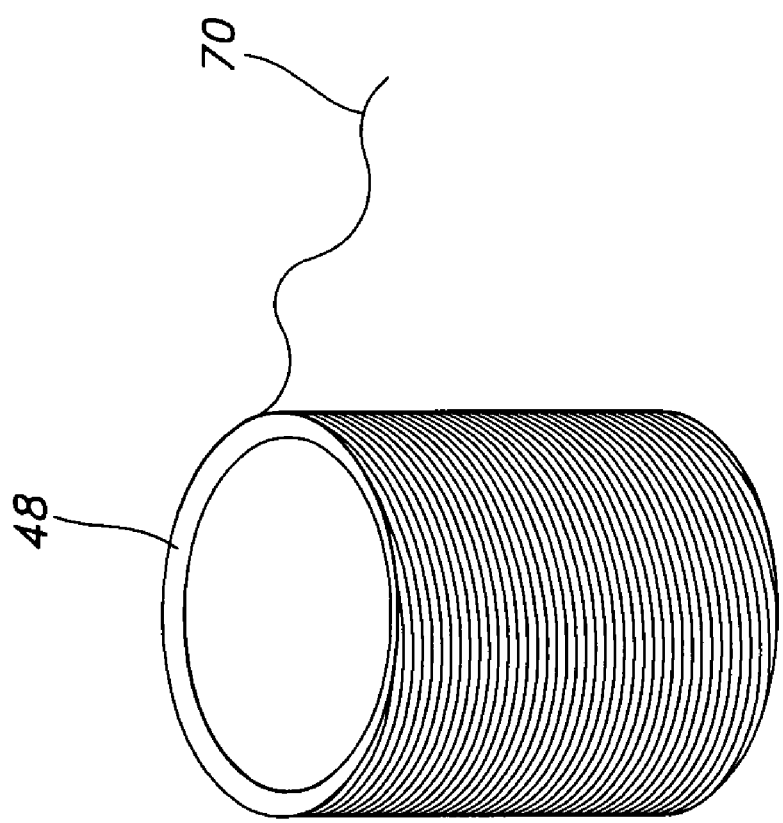
FIG. 4 is a perspective view of a hub with dental floss according to certain embodiments of the present invention.

Dental floss 70 is typically wrapped around a spool 48, as shown in FIG. 4. The spool preferably comprise a short section of an extruded tube and is preferably made from plastic. The diameter of the spool is selected to fit around the cylindrical protrusion. The spool with floss 70 wrapped on it are placed around the cylindrical protrusion and may rest on the annular base of the housing.

Figure 5:
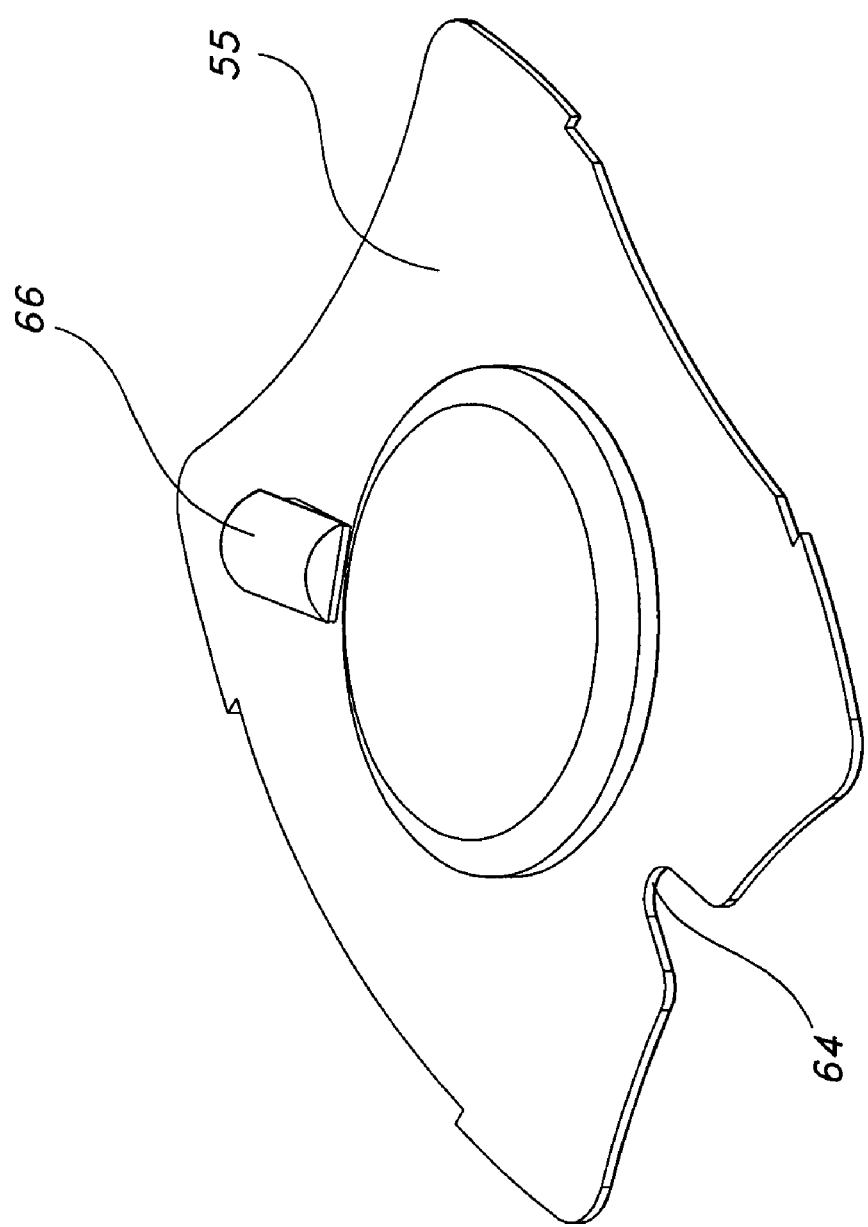
FIG. 5 is a perspective view of a dispenser cover according to certain embodiments of the present invention.
Figure 6:
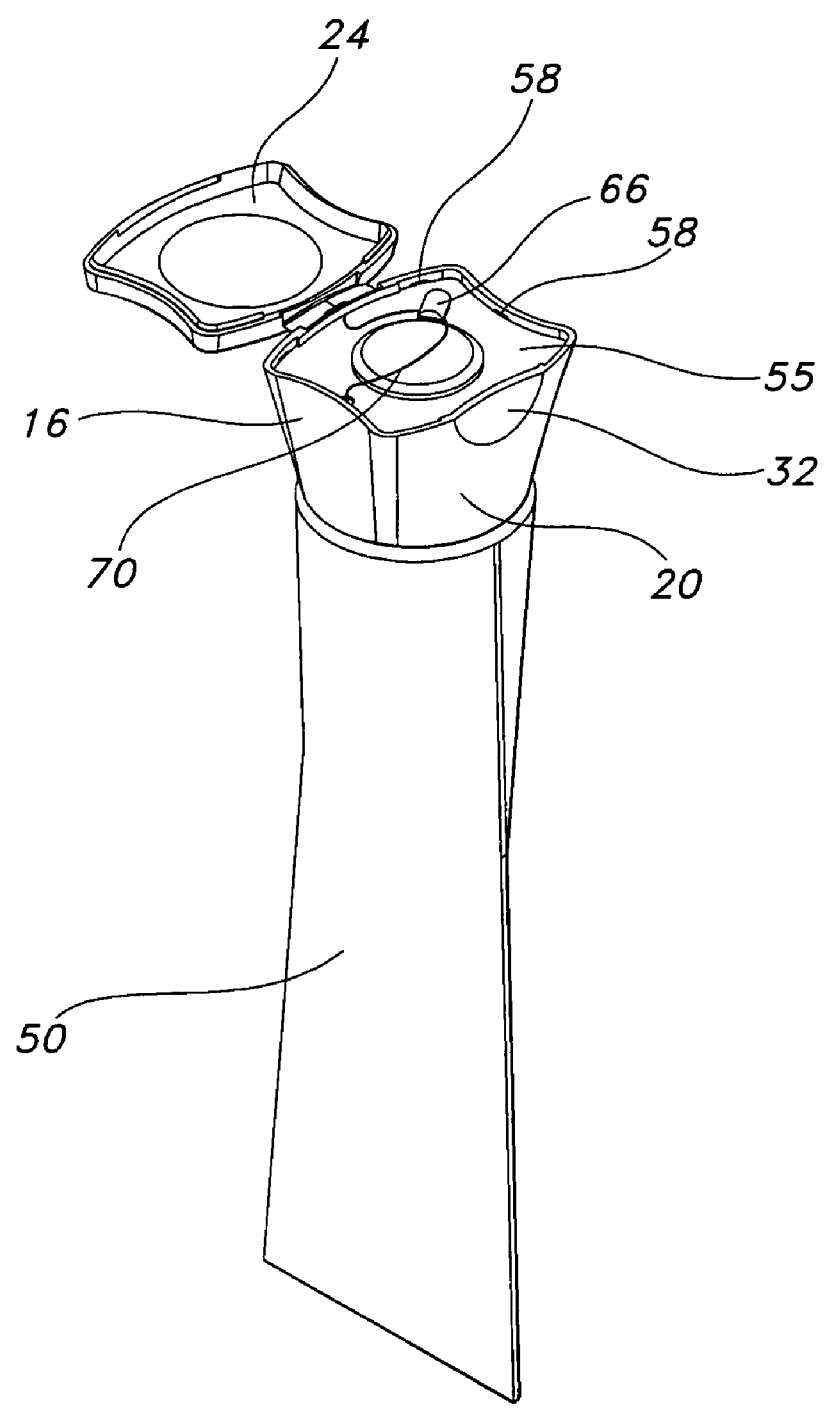
FIG. 6 is a perspective view of a dispenser cap according to certain embodiments of the present invention and a toothpaste tube.

A dispenser cover 55 preferably made from sheet metal may be located inside the dispenser cap, above the cylindrical protrusion according to certain embodiments of the invention and as shown in FIG. 5. The dispenser cap is preferably designed to conform to the shape of the exterior walls of the housing. As shown in FIG. 1, pressure tabs 58 are preferably located along the top, inside edge of the exterior housing walls. The pressure tabs extend slightly into the interior of the housing. The dispenser cover may be snap fit under the pressure tabs. Once placed under the pressure tabs, the dispenser cover may rest on the flat top surface 40 of the cylindrical protrusion or possibly along a flange 60 extending into the interior of the housing from the exterior walls, under the pressure tabs.

A small notch 64 is preferably located on a first end of the dispenser cover 55. The notch allows the floss to be dispensed from the spool located underneath the dispenser cover. A lance 66, which comprises a U-shaped cut of the dispenser cover is preferably located on the opposite end of the dispenser cover. The lance comprises a sharp interior edge and may be made from metal according to certain embodiments, allowing users to cut the dental floss when dispensed for use.

According to certain embodiments of the invention, the dispensing cap may comprise a cylindrical housing 72 as shown in FIGS. 8 and 9. The housing preferably comprises an upstanding protrusion 73 comprising upstanding walls 38 and a flat surface 40. The housing may comprise a cover 76 attached to the housing by a hinge 78. The cover preferably comprises a first surface 81 and a second surface 82. The cover 76 is preferably of the same general shape as the housing in order to cover the housing. As shown in FIGS. 8 and 9, for example, the cover may be generally circular in order to cover the cylindrical housing.

The cover may be pivoted along the hinge 78 to open or close the housing. A spool 48 of dental floss may preferably be placed around the upstanding protrusion. Once the spool is positioned within the housing, the cover 76 may be closed, covering the housing 72. When the cover is positioned to close the housing, the cover may preferably create a substantial friction fit with the housing. The cover may also be designed to comprise snap fit elements, creating a snap fit when closed. The cover may therefore be designed to allow replacement of the dental floss spool if desired. In the closed position, the first surface 81 of the cover is exterior to the housing and the second surface 82 is facing the interior of the housing.

The cover preferably comprises a notch 64 according to certain embodiments of the invention. The notch 64 is preferably located along the periphery of the cover 76, but may be located elsewhere if desired. When the cover is in the closed position, the dental floss may pass through the opening created by the notch, allowing access to the floss by users. A retention rod 83 is preferably located on the cover, at the end opposite the notch. The retention rod may be located between two parallel walls 86 that extend slightly away from the second surface of the cover. The retention rod therefore, is preferably recessed slightly when the cover is in the closed position.

A clip 88 comprising a lance 66 may preferably be attached to the retention rod 83. The clip 88 comprises a platform 89 for supporting the lance and a base 90. The platform is preferably generally flat and rectangular. The lance, according to certain embodiments of the invention, extends upward from the platform. The base is preferably located beneath the platform. The base comprises a flat portion and a upwardly curved end portion. The clip 88 is preferably made from metal or other suitable resilient material. The clip may be attached to the retention rod of the cover by forcing the curved portion of the base of the clip past the retention rod, securing the clip to the cover. The retention rod 83 prevents the clip from inadvertently disengaging from the cover. The lance is preferably positioned on the first surface 81 of the cover and can be used to cut the desired length of dental floss.

A second cover 94 or lid may be connected to the cover by a hinge 95 according to certain embodiments of the invention. Alternatively, the lid may be connected to the housing. The lid is preferably the same shape as the cover. When the lid is closed along the hinge, pressure applied to the top of the lid creates a friction fit. A lip 97 located on the front portion of the lid allows users to easily open the lid and gain access to the dental floss. The lid is preferably opened by placing the users thumb under the lip and applying upward pressure to the lid, releasing the friction fit. The lid may also be closed using a snap fit arrangement which will be understood by those skilled in the art.

The dispenser cap may be placed on top of a standard toothpaste tube 50 as shown in FIGS. 6, 7, 11 and 12. The dispenser cap is placed so that the hollow interior of the protrusion fits over the fluted cap of the toothpaste tube. The ribs on the inside of the walls of the protrusion mate with the fluted cap of the toothpaste tube. The dispenser cap may be depressed so the pressure tabs located along the annular base snap fit against the bottom edge of the fluted cap of the toothpaste tube.

Figure 7:
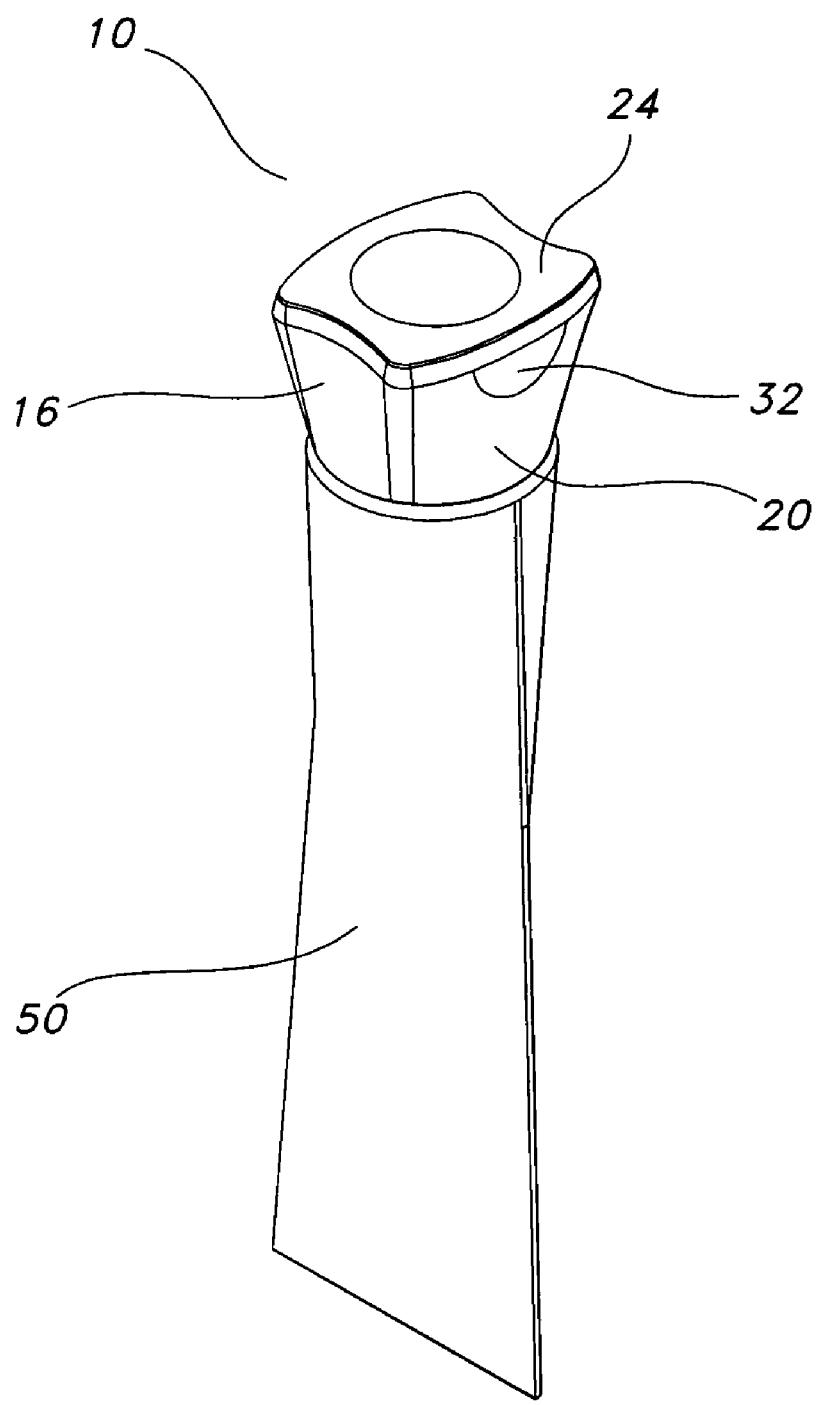
FIG. 7. is a perspective view of a dispenser cap according to certain embodiments of the present invention and a toothpaste tube.

Once the dispenser cap is secured to the toothpaste tube, the flip top lid may be opened by applying upward pressure to the lid. Dental floss 70 may be dispensed through the notch formed in the dispenser cover. The desired length of dental floss is selected by pulling the protruding portion and may be cut using the lance. The dispenser cap, which is affixed to the fluted cap of the toothpaste tube, may also be removed by unscrewing the entire dispenser cap to access the toothpaste inside the tube. The ergonomically designed housing according to certain embodiments of the invention may further facilitate such removal of the dispenser cap, providing a hand friendly design. After the user has cut the desired amount of floss and replaced the dispenser cap after accessing the toothpaste, the lid may be snap shut as shown in FIG. 7 and the entire toothpaste tube and dispenser cap may be placed on a flat surface with the lid of the dispenser cap facing down, creating a standup tube. It should be understood that if the dental floss is exhausted before the toothpaste, the dispenser cap may be replaced with a new dispenser cap containing dental floss. It should also be understood that the size of the housing and the amount of dental floss contained on the spool may be varied to accommodate different size toothpaste tubes.

According to certain embodiments of the invention, the housing may comprise a wall or walls extending upward from the inside edge of the annular base surface, forming a cylinder with no top surface. The cylinder may preferably be shaped to conform to the shape of the cylindrical opening of the toothpaste tube, allowing the dispenser cap to be secured to the open toothpaste tube. The user may then dispense toothpaste by opening the flip top lid of the dispenser cap and squeezing the tube. Such a configuration allows access to the toothpaste without unscrewing the dispenser cap from the toothpaste tube. In such a configuration, the lance may be located on the inside of the flip top lid, as a dispenser cover may not be needed.

According to certain embodiments of the invention, the dispenser cap 10 can be configured as the toothpaste cap itself. It should be understood by those skilled in the art that the dispenser cap would comprise mating threads to engage the toothpaste tube opening. Such a design may allow the sale of toothpaste tubes having the floss dispenser cap as the closure, eliminating the need for the toothpaste tube cap, as one item. Alternatively, the floss dispenser cap may be configured to fit on the end of any type of toothpaste tube including tubes with flip top lids, according to certain embodiments of the invention. The dispenser cap may be attached to toothpaste tubes with flip top lids by friction or snap fit elements, or both. The dispenser cap may be sold with the toothpaste tube as a single unit or as a separate item.

The dispenser cap according to certain embodiments of the invention may be attached to the toothpaste tube by a hinge, allowing the dispenser cap to serve as a flip top lid for the toothpaste tube.

What is claimed is:

1. A dental floss dispenser comprising:
   a housing comprising a base and a protrusion forming a cavity dimensioned to receive the cap of a toothpaste tube and having generally vertically oriented ribs along its interior;
   a spool of dental floss mounted for rotation on the protrusion;
   a cover connected to the housing by a first hinge, the cover enclosing the end of the housing opposite the cavity and comprising a notch and a cutting member whereby the end of the dental floss is threaded through the notch for removal; and
   a lid attached to the cover by a second hinge enclosing the cover;
   whereby the housing is capable of being attached to a toothpaste tube.

2. The dental floss dispenser of claim 1, wherein the housing is cylindrical.

3. The dental floss dispenser of claim 1, wherein the housing comprises two convex walls and two concave walls forming an ergonomically designed housing.

4. The dental floss dispenser of claim 1, wherein the cutting member comprises a metal lance attached to the cover for cutting the dental floss.

5. The dental floss dispenser of claim 1, further comprising a lip extending from the lid to facilitate opening of the lid.

6. The dental floss dispenser of claim 1, wherein the housing, cover and lid comprise plastic.

7. A dental floss dispenser for attachment to a tube of toothpaste comprising:
   a housing comprising a base and upstanding walls forming a cylindrical protrusion and a cavity beneath the protrusion dimensioned to receive the cap of a toothpaste tube, the interior portion of the upstanding walls having generally vertically oriented ribs;
   a spool of dental floss mounted for rotation on the cylindrical protrusion;
   a cover connected to the housing by a first hinge, the cover enclosing the end of the housing opposite the cavity and comprising a notch and a cutting member whereby the end of the dental floss is threaded through the notch for removal and cutting to a desired length by the cutting member; and a lid attached to the cover by a second hinge for opening and closing dispenser.

8. The dental floss dispenser of claim 7, wherein the housing is cylindrical.

9. The dental floss dispenser of claim 7, wherein the housing comprises two convex straight walls and two concave walls forming an ergonomically designed housing.

10. The dental floss dispenser of claim 7, wherein the cutting member comprises a metal lance attached to the cover for cutting the dental floss.

11. The dental floss dispenser of claim 7, further comprising a lip extending from the lid to facilitate opening of the cap.

12. The dental floss dispenser of claim 7, wherein the housing, cover and lid comprise plastic.

13. A dental floss dispenser comprising:

a housing comprising a base and a protrusion forming a cavity dimensioned to receive the cap of a toothpaste tube and having generally vertically oriented ribs along its interior;

a dental floss dispensing means within the housing for dispensing dental floss;

a cover connected to the housing by a first hinge, the cover enclosing the end of the housing opposite the cavity and comprising a notch and a cutting means for cutting the desired length of dental floss, whereby the end of the dental floss is threaded through the notch for removal; and a lid attached to the housing by a second hinge enclosing the cover;

whereby the housing is capable of being attached to a toothpaste tube.

14. The dental floss dispenser of claim 13, wherein the housing is cylindrical.

15. The dental floss dispenser of claim 13, wherein the housing comprises two convex walls and two concave walls forming an ergonomically designed housing.

16. The dental floss dispenser of claim 13, further comprising a lip extending from the lid to facilitate opening of the lid.

17. The dental floss dispenser of claim 13, wherein the housing, cover and lid comprise plastic.

18. An oral hygiene apparatus comprising:

a dental floss dispenser comprising a housing having a base and upstanding walls forming a protrusion and a cavity underneath the protrusion, the cavity comprising ribs;

dental floss mounted on the protrusion for dispensing;

a cover connected to the housing enclosing the end of the housing opposite the cavity and comprising a notch and a cutting member whereby the end of the dental floss is threaded through the notch for removal;

a lid attached to the dispenser by a hinge for opening and closing the dispenser; and a toothpaste tube comprising a rube body and a cap;

wherein the cavity of the dental floss dispenser is configured to fit over the toothpaste tube cap, attaching the dental floss dispenser to the toothpaste tube cap.

19. The oral hygiene apparatus of claim 18, wherein the ribs are generally vertically oriented.

20. The oral hygiene apparatus of claim 18, wherein the lid is attached to the cover.

* * * * *

UNITED STATES PATENT AND TRADEMARK OFFICE
CERTIFICATE OF CORRECTION

PATENT NO. : 7,243,663 B1 Page 1 of 1
APPLICATION NO. : 10/706740
DATED : July 17, 2007
INVENTOR(S) : J. Lyle Einstein, Jr. et al.

It is certified that error appears in the above-identified patent and that said Letters Patent is hereby corrected as shown below:

Column 2, line 25
Delete "combing" and insert --combining-- in place thereof

Column 3, line 49
Delete "tooth past" and insert --toothpaste-- in place thereof Column 3, line 65
Delete "comprises" and insert --comprise-- in place thereof Column 4, line 2
Delete "comprise" and insert --comprises-- in place thereof Column 5, line 25
Delete "users" and insert --user's-- in place thereof Claim 18, line 25
Delete "rube" and insert --tube-- in place thereof Signed and Sealed this Thirteenth Day of November, 2007

JON W. DUDAS
*Director of the United States Patent and Trademark Office*